(12) United States Patent
Savitsky et al.

(10) Patent No.: US 11,627,944 B2
(45) Date of Patent: Apr. 18, 2023

(54) ULTRASOUND CASE BUILDER SYSTEM AND METHOD

(71) Applicant: SonoSim, Inc., Santa Monica, CA (US)

(72) Inventors: Eric Savitsky, Malibu, CA (US); Gabriele Nataneli, Los Angeles, CA (US); Kresimir Petrinec, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/279,405

(22) Filed: Sep. 28, 2016

(65) Prior Publication Data

US 2017/0018204 A1    Jan. 19, 2017

Related U.S. Application Data

(63) Continuation-in-part of application No. 13/481,725, filed on May 25, 2012, now Pat. No. 10,026,338, which is a continuation-in-part of application No. 13/243,758, filed on Sep. 23, 2011, now Pat. No. 8,480,404, said application No. 13/481,725 is a continuation of application No. 11/720,515, filed as
(Continued)

(51) Int. Cl.
*A61B 8/00* (2006.01)
*G09B 23/28* (2006.01)

(52) U.S. Cl.
CPC .............. *A61B 8/56* (2013.01); *A61B 8/4254* (2013.01); *G09B 23/286* (2013.01)

(58) Field of Classification Search
CPC ........ A61B 8/56; G09B 23/286; G16H 50/50; G06F 19/321
See application file for complete search history.

(56) References Cited

U.S. PATENT DOCUMENTS

| 1,488,233 A | 3/1924 | Frederick |
| 1,762,937 A | 6/1930 | Stand |

(Continued)

FOREIGN PATENT DOCUMENTS

| EP | 1103223 A2 | 5/2001 |
| EP | 2801966 A1 | 11/2014 |

(Continued)

OTHER PUBLICATIONS

Chung, Gregory, "Effects of Simulation-Based Practice on Focused Assessment . . . ", Military Medicine, Oct. 2013, vol. 178.
(Continued)

*Primary Examiner* — Bill Thomson
*Assistant Examiner* — Helene Bor
(74) *Attorney, Agent, or Firm* — Cislo & Thomas, LLP

(57) ABSTRACT

A system for creating customized learning content for ultrasound simulators using materials from an existing library of curated content including images, volumetric data sets, and metadata, or otherwise acquired, overcoming numerous challenges to ultrasound education and training, including the ability to seamlessly create real-patient based ultrasound training curriculum, the creation of an expansive library that that represents multiple pathologic conditions, and the dissemination of training content to multiple users in an asynchronous manner.

11 Claims, 3 Drawing Sheets

Related U.S. Application Data application No. PCT/US2005/043155 on Nov. 30, 2005, now abandoned.

(60) Provisional application No. 62/234,585, filed on Sep. 29, 2015, provisional application No. 61/491,126, filed on May 27, 2011, provisional application No. 61/491,135, filed on May 27, 2011, provisional application No. 61/491,131, filed on May 27, 2011, provisional application No. 61/491,138, filed on May 27, 2011, provisional application No. 60/631,488, filed on Nov. 30, 2004.

(56) References Cited

U.S. PATENT DOCUMENTS

| | | | |
|---|---|---|---|
| 2,019,121 A | 10/1935 | De Rewal | |
| 2,112,019 A | 3/1938 | Gyger | |
| 2,127,610 A | 8/1938 | Moore | |
| 2,705,049 A | 3/1955 | Brooks | |
| 2,705,307 A | 3/1955 | Edson | |
| 2,722,947 A | 11/1955 | Sragal | |
| 2,886,316 A | 5/1959 | Ayala | |
| 4,040,171 A | 8/1977 | Cline et al. | |
| 4,838,863 A | 6/1989 | Allard et al. | |
| 4,838,869 A | 6/1989 | Allard | |
| 4,994,034 A | 2/1991 | Botich et al. | |
| 5,231,381 A | 7/1993 | Duwaer | |
| 5,513,992 A | 5/1996 | Refait | |
| 5,609,485 A * | 3/1997 | Bergman | G01S 7/52055 128/916 |
| 5,678,565 A | 10/1997 | Sarvazyan | |
| 5,689,443 A | 11/1997 | Ramanathan | |
| 5,701,900 A | 12/1997 | Shehada et al. | |
| 5,704,791 A | 1/1998 | Giiiio | |
| 5,755,577 A | 5/1998 | Gillio | |
| 5,767,839 A | 6/1998 | Rosenberg | |
| 5,776,062 A | 7/1998 | Nields | |
| 5,791,908 A | 8/1998 | Gillio | |
| 5,800,177 A | 9/1998 | Gillio | |
| 5,800,178 A | 9/1998 | Gillio | |
| 5,800,179 A | 9/1998 | Bailey | |
| 5,800,350 A | 9/1998 | Coppieson et al. | |
| 5,827,942 A | 10/1998 | Madsen et al. | |
| 5,882,206 A | 3/1999 | Gillio | |
| 5,889,237 A | 3/1999 | Makinwa | |
| 5,934,288 A | 8/1999 | Avila et al. | |
| 6,001,472 A | 12/1999 | Ikeda et al. | |
| 6,048,312 A | 4/2000 | Ishrak et al. | |
| 6,063,030 A | 5/2000 | Vara et al. | |
| 6,068,597 A | 5/2000 | Lin | |
| 6,074,213 A | 6/2000 | Hon | |
| 6,113,395 A | 9/2000 | Hon | |
| 6,117,078 A * | 9/2000 | Lysyansky | G01S 7/52036 434/262 |
| 6,122,538 A | 9/2000 | Sliwa, Jr. et al. | |
| 6,156,213 A | 12/2000 | Dudley et al. | |
| 6,193,657 B1 | 2/2001 | Drapkin | |
| 6,267,599 B1 | 7/2001 | Bailey | |
| 6,468,212 B1 | 10/2002 | Scott et al. | |
| 6,502,756 B1 | 1/2003 | Fåhraeus | |
| 6,511,427 B1 | 1/2003 | Sliwa, Jr. et al. | |
| 6,548,768 B1 | 4/2003 | Pettersson et al. | |
| 6,570,104 B1 | 5/2003 | Ericson et al. | |
| 6,654,000 B2 | 11/2003 | Rosenberg | |
| 6,663,008 B1 | 12/2003 | Pettersson et al. | |
| 6,665,554 B1 | 12/2003 | Charles et al. | |
| 6,666,376 B1 | 12/2003 | Ericson | |
| 6,667,695 B2 | 12/2003 | Pettersson et al. | |
| 6,674,427 B1 | 1/2004 | Pettersson et al. | |
| 6,689,966 B2 | 2/2004 | Wiebe | |
| 6,693,626 B1 | 2/2004 | Rosenberg | |
| 6,694,163 B1 | 2/2004 | Vining | |
| 6,698,660 B2 | 3/2004 | Fåhraeus et al. | |
| 6,714,213 B1 | 3/2004 | Lithicum et al. | |
| 6,714,901 B1 | 3/2004 | Cotin et al. | |
| 6,719,470 B2 | 4/2004 | Berhin | |
| 6,722,574 B2 | 4/2004 | Skantze et al. | |
| 6,732,927 B2 | 5/2004 | Olsson et al. | |
| 6,750,877 B2 | 6/2004 | Rosenberg et al. | |
| 6,780,016 B1 | 8/2004 | Toly | |
| 6,816,148 B2 | 11/2004 | Mallett et al. | |
| 6,836,555 B2 | 12/2004 | Ericson et al. | |
| 6,854,821 B2 | 2/2005 | Ericson et al. | |
| 6,864,880 B2 | 3/2005 | Hugosson et al. | |
| 6,878,062 B2 | 4/2005 | Bjorklund et al. | |
| 6,896,650 B2 | 5/2005 | Tracey et al. | |
| 6,916,283 B2 | 7/2005 | Tracey et al. | |
| 6,927,916 B2 | 8/2005 | Craven-Bartle | |
| 6,929,183 B2 | 8/2005 | Pettersson | |
| 6,929,481 B1 | 8/2005 | Alexander et al. | |
| 6,947,033 B2 | 9/2005 | Fåhraeus et al. | |
| 6,958,747 B2 | 10/2005 | Sahlberg et al. | |
| 6,966,495 B2 | 11/2005 | Lynggaard et al. | |
| 6,992,655 B2 | 1/2006 | Ericson et al. | |
| 7,002,559 B2 | 2/2006 | Ericson | |
| 7,035,429 B2 | 4/2006 | Andreasson | |
| 7,037,258 B2 | 5/2006 | Chatenever et al. | |
| 7,050,653 B2 | 5/2006 | Edso et al. | |
| 7,054,487 B2 | 5/2006 | Ericson et al. | |
| 7,072,529 B2 | 7/2006 | Hugosson et al. | |
| 7,089,308 B2 | 8/2006 | Fransson et al. | |
| 7,094,977 B2 | 8/2006 | Ericson et al. | |
| 7,110,604 B2 | 9/2006 | Olsson | |
| 7,120,320 B2 | 10/2006 | Petterson et al. | |
| 7,121,465 B2 | 10/2006 | Rignell | |
| 7,127,682 B2 | 10/2006 | Sandstrom et al. | |
| 7,143,952 B2 | 12/2006 | Ericson | |
| 7,145,556 B2 | 12/2006 | Pettersson | |
| 7,154,056 B2 | 12/2006 | Bergqvist et al. | |
| 7,162,087 B2 | 1/2007 | Bryborn | |
| 7,167,164 B2 | 1/2007 | Ericson et al. | |
| 7,172,131 B2 | 2/2007 | Pettersson et al. | |
| 7,175,095 B2 | 2/2007 | Pettersson et al. | |
| 7,176,896 B1 | 2/2007 | Fahraeus et al. | |
| 7,180,509 B2 | 2/2007 | Fermgard et al. | |
| 7,195,166 B2 | 3/2007 | Olsson et al. | |
| 7,202,861 B2 | 4/2007 | Lynggaard | |
| 7,202,963 B2 | 4/2007 | Wiebe et al. | |
| 7,239,306 B2 | 7/2007 | Fahraeus et al. | |
| 7,246,321 B2 | 7/2007 | Bryborn et al. | |
| 7,248,250 B2 | 7/2007 | Pettersson et al. | |
| 7,249,256 B2 | 7/2007 | Hansen et al. | |
| 7,249,716 B2 | 7/2007 | Bryborn | |
| 7,254,839 B2 | 8/2007 | Fahraeus et al. | |
| 7,263,710 B1 * | 8/2007 | Hummel, Jr. | G06F 19/324 725/86 |
| 7,278,017 B2 | 10/2007 | Skantze | |
| 7,281,668 B2 | 10/2007 | Pettersson et al. | |
| 7,283,676 B2 | 10/2007 | Olsson | |
| 7,293,697 B2 | 11/2007 | Wiebe et al. | |
| 7,295,193 B2 | 11/2007 | Fahraeus | |
| 7,296,075 B2 | 11/2007 | Lynggaard | |
| 7,321,692 B2 | 1/2008 | Bryborn et al. | |
| 7,333,947 B2 | 2/2008 | Wiebe et al. | |
| 7,345,673 B2 | 3/2008 | Ericson et al. | |
| 7,353,393 B2 | 4/2008 | Hansen et al. | |
| 7,356,012 B2 | 4/2008 | Wiebe et al. | |
| 7,371,068 B2 | 5/2008 | Lloyd et al. | |
| 7,382,361 B2 | 6/2008 | Burstrom et al. | |
| 7,385,595 B2 | 6/2008 | Bryborn et al. | |
| 7,408,536 B2 | 8/2008 | Hugosson et al. | |
| 7,415,501 B2 | 8/2008 | Burstrom | |
| 7,418,160 B2 | 8/2008 | Lynggaard | |
| 7,422,154 B2 | 9/2008 | Ericson | |
| 7,441,183 B2 | 10/2008 | Burstrom et al. | |
| 7,457,413 B2 | 11/2008 | Thuvesholmen et al. | |
| 7,457,476 B2 | 11/2008 | Olsson | |
| 7,543,753 B2 | 6/2009 | Pettersson | |
| 7,588,191 B2 | 9/2009 | Pettersson et al. | |
| 7,600,693 B2 | 10/2009 | Pettersson | |
| 7,649,637 B2 | 1/2010 | Wiebe et al. | |
| 7,670,070 B2 | 3/2010 | Craven-Bartle | |
| 7,672,513 B2 | 3/2010 | Bjorklund et al. | |

(56) References Cited

U.S. PATENT DOCUMENTS

| | | | |
|---|---|---|---|
| 7,701,446 B2 | 4/2010 | Sahlberg et al. | |
| 7,710,408 B2 | 5/2010 | Ericson | |
| 7,751,089 B2 | 7/2010 | Fahraeus et al. | |
| 7,753,283 B2 | 7/2010 | Lynggaard | |
| 7,777,777 B2 | 8/2010 | Bowman et al. | |
| 7,788,315 B2 | 8/2010 | Johansson | |
| 7,794,388 B2 | 9/2010 | Draxinger et al. | |
| 7,806,696 B2 | 10/2010 | Alexander et al. | |
| 7,833,018 B2 | 11/2010 | Alexander et al. | |
| 7,850,454 B2 | 12/2010 | Toly | |
| 7,857,626 B2 | 12/2010 | Toly | |
| 7,871,850 B2 | 1/2011 | Park | |
| 7,931,470 B2 | 4/2011 | Alexander et al. | |
| 8,244,506 B2 | 8/2012 | Butsev et al. | |
| 8,294,972 B2 | 10/2012 | Chung | |
| 8,428,326 B2 | 4/2013 | Falk et al. | |
| 8,480,404 B2 | 7/2013 | Savitsky | |
| 8,480,406 B2 | 7/2013 | Alexander et al. | |
| 8,556,635 B2 * | 10/2013 | Toly | G09B 23/285 434/262 |
| 8,721,344 B2 | 5/2014 | Marmaropoulos et al. | |
| 9,128,116 B2 | 9/2015 | Welch et al. | |
| 9,251,721 B2 | 2/2016 | Lampotang | |
| 9,436,993 B1 | 9/2016 | Stolka et al. | |
| 9,870,721 B2 | 1/2018 | Savitsky et al. | |
| 9,911,365 B2 * | 3/2018 | Siassi | G09B 23/28 |
| 10,052,010 B2 | 8/2018 | Feddema | |
| 10,132,015 B2 | 11/2018 | Woodruff et al. | |
| 11,011,077 B2 | 5/2021 | Garcia Kilroy | |
| 2001/0031920 A1 | 10/2001 | Kaufman et al. | |
| 2002/0076581 A1 | 6/2002 | McCoy | |
| 2002/0076681 A1 | 6/2002 | Leight et al. | |
| 2002/0088926 A1 | 7/2002 | Prasser | |
| 2002/0099310 A1 | 7/2002 | Kimchy et al. | |
| 2002/0168618 A1 | 11/2002 | Anderson et al. | |
| 2002/0173721 A1 | 11/2002 | Grunwald et al. | |
| 2004/0043368 A1 | 3/2004 | Hsieh et al. | |
| 2004/0087850 A1 | 5/2004 | Okerlund et al. | |
| 2005/0119569 A1 | 6/2005 | Ohtake | |
| 2005/0181342 A1 | 8/2005 | Toly | |
| 2005/0214726 A1 | 9/2005 | Feygin et al. | |
| 2005/0228617 A1 | 10/2005 | Kerwin et al. | |
| 2005/0283075 A1 | 12/2005 | Ma et al. | |
| 2006/0020204 A1 | 1/2006 | Serra et al. | |
| 2006/0098010 A1 | 5/2006 | Dwyer et al. | |
| 2007/0088213 A1 | 4/2007 | Poland | |
| 2007/0161904 A1 | 7/2007 | Urbano | |
| 2007/0232907 A1 | 10/2007 | Pelissier et al. | |
| 2007/0236514 A1 | 10/2007 | Augusanto | |
| 2007/0238085 A1 * | 10/2007 | Colvin | G09B 19/00 434/365 |
| 2008/0009743 A1 | 1/2008 | Hayasaka | |
| 2008/0137071 A1 | 6/2008 | Chow | |
| 2008/0187896 A1 | 8/2008 | Savitsky | |
| 2008/0200807 A1 | 8/2008 | Wright et al. | |
| 2008/0204004 A1 | 8/2008 | Anderson | |
| 2008/0269606 A1 | 10/2008 | Matsumura | |
| 2008/0294096 A1 | 11/2008 | Uber et al. | |
| 2008/0312884 A1 | 12/2008 | Hostettler et al. | |
| 2009/0006419 A1 | 1/2009 | Savitsky | |
| 2009/0043195 A1 | 2/2009 | Poland | |
| 2009/0046912 A1 | 2/2009 | Hostettler | |
| 2009/0130642 A1 | 5/2009 | Tada et al. | |
| 2009/0209859 A1 | 8/2009 | Tsujita et al. | |
| 2009/0266957 A1 | 10/2009 | Cermak | |
| 2009/0305213 A1 | 12/2009 | Burgkart et al. | |
| 2009/0311655 A1 | 12/2009 | Karkanias et al. | |
| 2010/0055657 A1 * | 3/2010 | Goble | G09B 23/286 434/262 |
| 2010/0104162 A1 | 4/2010 | Falk et al. | |
| 2010/0179428 A1 * | 7/2010 | Pedersen | A61B 8/00 600/443 |
| 2010/0268067 A1 | 10/2010 | Razzaque et al. | |
| 2010/0277422 A1 | 11/2010 | Muresianu et al. | |
| 2011/0010023 A1 | 1/2011 | Kunzig et al. | |
| 2011/0306025 A1 | 12/2011 | Sheehan et al. | |
| 2012/0021993 A1 | 1/2012 | Kim et al. | |
| 2012/0058457 A1 | 3/2012 | Savitsky | |
| 2012/0143142 A1 | 6/2012 | Klein | |
| 2012/0150797 A1 * | 6/2012 | Landy | G06F 16/254 707/610 |
| 2012/0179039 A1 | 7/2012 | Pelissier et al. | |
| 2012/0200977 A1 | 8/2012 | Nestler | |
| 2012/0219937 A1 | 8/2012 | Hughes et al. | |
| 2012/0237102 A1 | 9/2012 | Savitsky et al. | |
| 2012/0237913 A1 * | 9/2012 | Savitsky | A61B 8/58 434/262 |
| 2012/0238875 A1 | 9/2012 | Savitsky et al. | |
| 2012/0251991 A1 | 10/2012 | Savitsky et al. | |
| 2013/0046523 A1 | 2/2013 | Van Dinther | |
| 2013/0064036 A1 | 3/2013 | Lee et al. | |
| 2013/0065211 A1 | 3/2013 | Amso et al. | |
| 2013/0137989 A1 | 5/2013 | Chen | |
| 2013/0158411 A1 | 6/2013 | Miyasaka | |
| 2013/0179306 A1 | 7/2013 | Want et al. | |
| 2013/0236872 A1 | 9/2013 | Laurusonis et al. | |
| 2014/0087347 A1 | 3/2014 | Tracy | |
| 2014/0114194 A1 | 4/2014 | Kanayama et al. | |
| 2014/0119645 A1 | 5/2014 | Zimet | |
| 2014/0120505 A1 | 5/2014 | Rios et al. | |
| 2014/0170620 A1 | 6/2014 | Savitsky et al. | |
| 2014/0228685 A1 | 8/2014 | Eelbode | |
| 2014/0272878 A1 | 9/2014 | Shim et al. | |
| 2015/0056591 A1 | 2/2015 | Tepper et al. | |
| 2015/0078639 A1 * | 3/2015 | Hausotte | G06T 7/0014 382/128 |
| 2015/0084897 A1 | 3/2015 | Nataneli et al. | |
| 2015/0086956 A1 | 3/2015 | Savitsky et al. | |
| 2015/0140538 A1 | 5/2015 | Savitsky et al. | |
| 2015/0154890 A1 | 6/2015 | Savitsky et al. | |
| 2015/0213731 A1 | 7/2015 | Sato | |
| 2016/0314716 A1 | 10/2016 | Grubbs | |
| 2016/0328998 A1 | 11/2016 | Pedersen et al. | |
| 2017/0028141 A1 | 2/2017 | Fiedler et al. | |
| 2017/0035517 A1 | 2/2017 | Geri | |
| 2017/0046985 A1 | 2/2017 | Hendrickson et al. | |
| 2017/0110032 A1 | 4/2017 | O'Brien | |
| 2017/0270829 A1 | 9/2017 | Bauss | |
| 2018/0197441 A1 | 7/2018 | Rios | |
| 2018/0366034 A1 | 12/2018 | Casals Gelpi | |
| 2019/0057620 A1 | 2/2019 | Eggert | |
| 2019/0231436 A1 | 8/2019 | Panse | |
| 2019/0321657 A1 | 10/2019 | Hale | |
| 2020/0126449 A1 | 4/2020 | Horst | |
| 2020/0138518 A1 | 5/2020 | Lang | |
| 2021/0128125 A1 | 5/2021 | Sitti et al. | |
| 2021/0186311 A1 | 6/2021 | Levy et al. | |

FOREIGN PATENT DOCUMENTS

| | | |
|---|---|---|
| RU | 2127610 C1 | 3/1999 |
| RU | 1994040171 | 11/2014 |
| WO | 2006060406 A1 | 6/2006 |

OTHER PUBLICATIONS

Aligned Management Associates, Inc., Corporate home page describing organizing committee, overview, Procedicus MIST[trademark]-suturing module 30.0, 6 pgs., obtained from website Sep. 6, 2004.

American Academy of Emergency Medicine, conference: 11th annual scientific assembly preconference ultrasound courts, http://www.aaem.org/education/scientificassembly/sa05/precon/ultrasound.shtml, 6 pgs., obtained from website Feb. 16, 2005.

Barbosa, J. et al., "Computer education in emergency medicine residency programs," http://www.med-ed-online.org/res00002.htm, 8 pgs., obtained from website Sep. 6, 2004.

Brannam, L et al, "Emergency nurses utilization of ultrasound guidance for placement of peripheral intravenous lines in difficult-access patients," Acad Emerg Med, 11(12):1361-1363, Dec. 2004.

Calvert, N. et al., "The effectiveness and cost-effectiveness of ultrasound locating devices for central venous access: a systematic

(56) References Cited

OTHER PUBLICATIONS review and economic evaiuation/executive summary," Health Tech Assess 2003, 7(12), 4 pgs.

Center for Human Simulation, corporate home page describing overview/people, http://www.uchsc.edu, 7 pgs, obtained from website Sep. 6, 2004.

CIMIT News, "The medical access program: new CIMIT initiative to benefit underserved patients/partners telemedicine and CIMIT launch new initiative: stay connected, be healthy/highlights: operating room of the future plug-and-play project," http://www.cimit.org, Jan. 2005; vol. II(2), 2 pgs., obtained from website Mar. 1, 2005.

Colt, H. G. et al., "Virtual reality bronchoscopy simulation: a revolution in procedural training," Chest 2001; 120:1333-1339.

Computer Motion, "About computer motion: technology to enhance surgeons capabilities, improve patient outcomes and reduce healthcare costs/corporate alliances/products solutions for surgical innovation/training on the da Vinci[registered] surgical system-introduction," 2002 Computer Motion, http://www.computermotion.com, 6 pgs.

Delp, Setai, "Surgical simulation—an emerging technology for training in emergency medicine," Presence, 6 (2):147-159, Apr. 1997 (abstract).

Dorner, R. et. al., "Synergies between interactive training simulations and digital storytelling: a component-based framework," Computer Graphics, 26(1):45-55, Feb. 2002 (abstract).

Duque, D. and Kessler S., "Ultrasound guided vascular access," Amer Coli Emerg Phy., http://www.nyacep.org/education/articles/ultrasound%20vascular%20access.htm, 2 pgs, obtained from website May 11, 2005.

Espinet, A. and Dunning J., "Does ultrasound-guided central line insertion reduce complications and time to placement in elective patients undergoing cardiac surgery," Inter Cardiovascular Thoracic Surg, 3:523-527, 2004; http:/licvts.ctsnetjournals.org/cgi/content/full/3/3/523, 6 pgs, obtained from website May 11, 2005 (abstract).

Gallagher, A. G. et al., "Virtual reality training for the operating room and cardiac catheterization laboratory," Lancet, 364:1538-1540, Oct. 23, 2004.

Gallagher, A. G. et al., "Psychomotor skills assessment in practicing surgeons experienced in performing advanced laparoscopic procedures," AM Coli Surg, 197(3):479-488, Sep. 2003.

Gausche, M. et al., "Effect on out-of-hospital pediatric endotracheal Intubation on survival and neurological outcome: a controlled clinical trial," JAMA, 283(6)783-790, Feb. 9, 2000.

Gore, D. C. and Gregory, S. R., "Historical perspective on medical errors: Richard Cabot and the Institute of Medicine," J Amer Coli Surg, 197(4), 5 pgs, Oct. 2003.

Grantcharov, T. P. et al., "Randomized clinical trial of virtual reality simulation for laparoscopic skills training," Br J Surg, 91(2):146-150, Feb. 1, 2004 (abstract).

Grantcharov, T. P. et al., "Learning curves and impact of previous operative experience on performance on a virtual reality simulator to test laparoscopic surgical skills," Am J Surg, 185(2):146-149, Feb. 1, 2004 (abstract).

Haluck, R. S., et al., "Are surgery training programs ready for virtual reality A survey of program directors in general surgery," Arch Surg, 135(7):786-792, Jul. 1, 2000.

Helmreich, R. L., "On error management: lessons from aviation," BMJ, 320:781-785, Mar. 2000.

Huckman, R. S. and Pisano, G. P., "Turf battles in coronary revascularization," N Engl J Med, http://www.nejm.org, 4 pgs. 352(9):857-859, Mar. 3, 2005.

Immersion Corporation, URL: http://www.immersion.com/corporate/products/, corporate home page describing Immersions surgical training simulators—"Wireless Data Glove: The CyberGlove[registered]II System," 5 pgs, obtained from the website Nov. 17, 2005 and Jan. 24, 2008.

injuryboard.com, "Reducing complications associated with central vein catheterization," URSL: http://www.injuryboard.com/view.cfm/Article=668, 5 pgs, obtained from website May 11, 2005.

INTERSENSE, home page listing motion tracking products, http://www.isense.com/prodcuts.aspxid=42,1 pg, obtained from website Jan. 24, 2008.

Jemmett, M. E., et. al., "Unrecognized misplacement of endotracheal tubes in a mixed urban to rural emergency medical services setting," Acad Emerg Med, 10(9):961-964, Sep. 2003.

Katz, S. H. and Falk, J. L., "Misplaced endotrachial tubes by paramedics in an urban medical services system," Annals Emerg Med, 37:32-37, Jan. 2001.

Lewis, R., "Educational research: time to reach the bar, not lower it," Acad Emerg Med, 12(3):247-248, Mar. 2005.

Liu, A. et, al., "A survey of surgical simulation: applications, technology, and education," Presence, 12(6):1-45, Dec. 2003.

Manchester Visulations Centre, "Webset project-bringing 3D medical training tools to the WWW," http://www.sve.man.ac.uklmvc/research/previous/website, 3 pgs, obtained from the website Sep. 8, 2004.

Mclellan, H., "Virtual realities," Mclellan Wyatt Digital, 33 pgs.

Medical Simulation Corporation, corporate home page describing management team/frequently asked questions, http://www.medsimulation.com/about_msc/key_employees.asp, 7 pgs, obtained from website Nov. 25, 2004.

Medtronic, "The StealthStation[registered] treatment guidance system," the corporate home page describing the company fact sheet and profile; http://www.medtronic.com/Newsroom, 4 pgs, obtained from website Mar. 5, 2005.

Mort, T. C., "Emergency tracheal intubation: complications associated with repeated laryngoscopic attempts," Anesth Analg, 99(2):607-613, Aug. 2004, 1 pg, obtained from website Sep. 8, 2004 (abstract).

Nazeer, S. R., et al., "Ultrasound-assisted paracentesis performed by emergency physicians v.s. the traditional technique: a prospective, randomized study," Amer J of Emer Med, 23:363-367, 2005.

NCA Medical Simulation Center, Tutorial-simulation for medical training, http://Simcen.usuhs.millmiccaie, 4 pgs, 2003.

Next Dimension Imaging, "Products-Anatomy Analyzer 2," http://www.nexted.com/anatomyanalyzer.asp, 2 pgs, obtained from website Dec. 7, 2004.

Norris, T. E. et al., "Teaching procedural skills," J General Internal Med. 12(S2):S64-S70, Apr. 1997.

On the Net Resources-Education and Training, URL: http://www.hitl.washington.edu/projects/knowledge_base/education.html, corporate home page regarding internet sites regarding education and training, 16 pgs, obtained from website Jan, 8, 2005.

Osberg, K. M., "Virtual reality and education: a look at both sides of the sword," http://www.hitl.washington.edu/publications/r-93-7/, 19 pgs, Dec. 14, 1992, obtained from website Jan. 21, 2008.

Osmon, S. et al., "Clinical investigations: reporting of medical errors: an intensive care unit experience," Grit Care Med. 32(3), 13 pgs, Mar. 2004.

Ponder, M., et al., "Immersive VR decision training: telling Interactive stories featuring advanced human simulation technologies," Eurographics Association 2003, 10 pgs.

Primal, corporate home page describing resources for teaching healthcare practitioners, 2 pgs, obtained from website.

Prystowsky, J. B. et al., "A virtual reality module for intravenous catheter placement," Am J Surg 1999; 177 (2):171-175 (abstract).

Reachin, "Medical Training Development Centre/Reachin technologies AB has entered into a corporation with Mentice AB," Jan. 20, 2004, 4 pgs, obtained from website Nov. 9, 2004.

Rothschild, J. M., "Ultrasound guidance of central vein catheterization," NCBI, Nat Lib Med, www.ncbi.nlm.nih.gov/books/, HSTAT 21, 6 pgs, obtained from website May 11, 2005.

Rowe, R. and Cohen, R. A., "An evaluation of a virtual reality airway simulator," Anesth Analg 2002, 95:62-66.

Sensable Technologies, "PHANTOM Omni Haptic Device," 2 pgs, http://www.sensable.com/haptic-ohantom-omni.htm., obtained from website Jan. 24, 2008.

Shaffer, K., "Becoming a physician: teaching anatomy in a digital age," NEJM, Sep. 23, 2004; 351(13):1279-81 (extract of first 100 words—no abstract).

\* cited by examiner

ULTRASOUND CASE BUILDER SYSTEM AND METHOD

CROSS-REFERENCES TO RELATED APPLICATIONS

This patent application claims the benefit of U.S. Provisional Application No. 62/234,585, filed on Sep. 29, 2015.

This patent application is also a continuation-in-part of U.S. patent application Ser. No. 13/481,725, filed May 25, 2012, which is a continuation-in-part of U.S. patent application Ser. No. 13/243,758 filed Sep. 23, 2011 for Multimodal Ultrasound Training System, now U.S. Pat. No. 8,480,404, which is a continuation of U.S. Ser. No. 11/720,515 filed May 30, 2007 for Multimodal Medical Procedure Training System, now abandoned, which is the national stage entry of PCT/US05/43155, entitled "Multimodal Medical Procedure Training System" and filed Nov. 30, 2005, which claims priority to U.S. Provisional Patent Application No. 60/631,488, entitled Multimodal Emergency Medical Procedural Training Platform and filed Nov. 30, 2004.

Parent U.S. patent application Ser. No. 13/481,725, filed May 25, 2012, also claims the benefit of U.S. Provisional Application Ser. No. 61/491,126 filed May 27, 2011 for Data Acquisition, Reconstruction, and Simulation; U.S. Provisional Application Ser. No. 61/491,131 filed May 27, 2011 for Data Validator; U.S. Provisional Application Ser. No. 61/491,134 filed May 27, 2011 for Peripheral Probe with Six Degrees of Freedom Plus 1; U.S. Provisional Application Ser. No. 61/491,135 filed May 27, 2011 for Patient-Specific Advanced Ultrasound Image Reconstruction Algorithms; and U.S. Provisional Application Ser. No. 61/491,138 filed May 27, 2011 for System and Method for Improving Acquired Ultrasound-Image Review.

Applicant incorporates into the present application all disclosures of each of the foregoing patent applications by this reference.

BACKGROUND OF THE INVENTION

The ability to export medical data from an ultrasound machine to a computer system has recently aided the emergence of a new generation of sophisticated raining simulators, which are routinely used by wide audiences of medical learners. These simulators can thereby deliver compelling experiences where users can interact directly with real patient data and learn how to diagnose life-threatening pathologies within the confines of a training center or even the comfort of one's home. The realism of these new simulation technologies has led to a sharp improvement in the quality and effectiveness of today's training solutions. At the current state of the art, however, the case libraries of medical data that feed into the simulators are acquired and curated by a select number of experts working directly with the developers of such training solutions. One improvement of the present invention, therefore, involves a new service-oriented architecture that allows a wider audience of interested parties to author, customize, and share training content with a community of learners.

DESCRIPTION OF THE PREFERRED EMBODIMENTS

Figure 1:
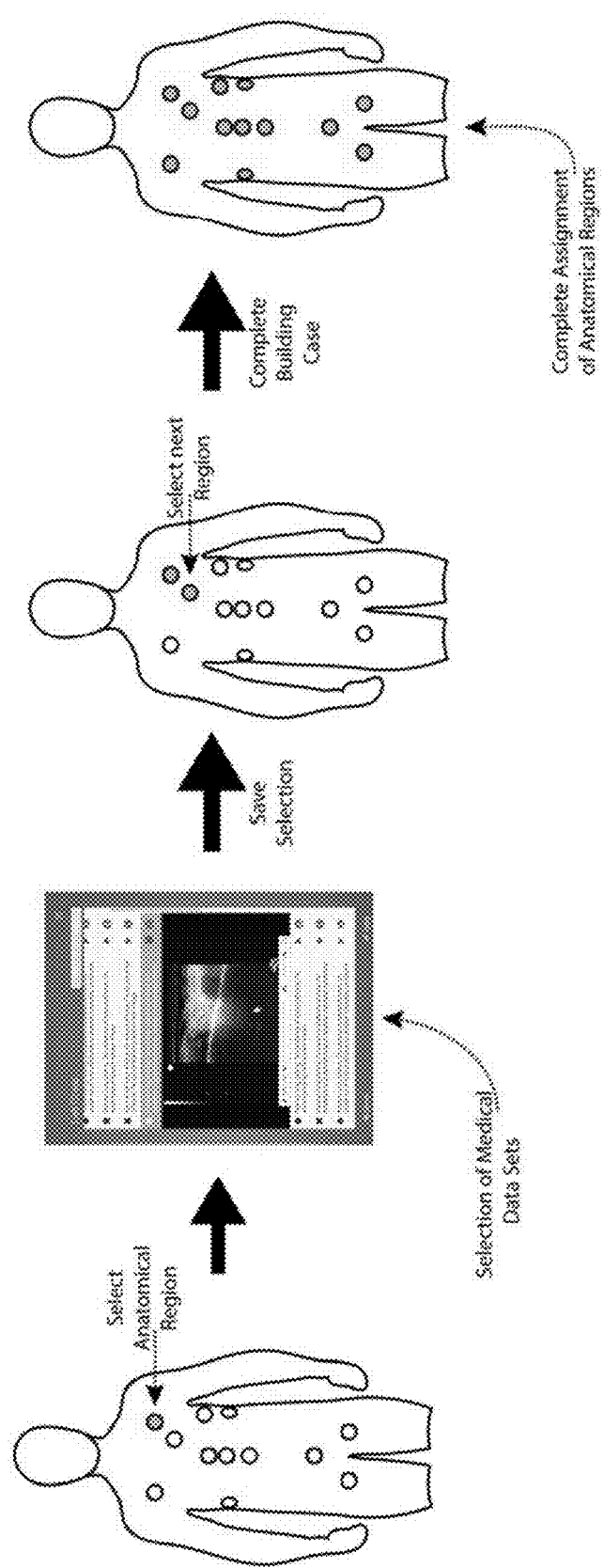
FIG. 1 is a diagram showing selection of data sets to build a case using one embodiment of the present invention.
Figure 2:
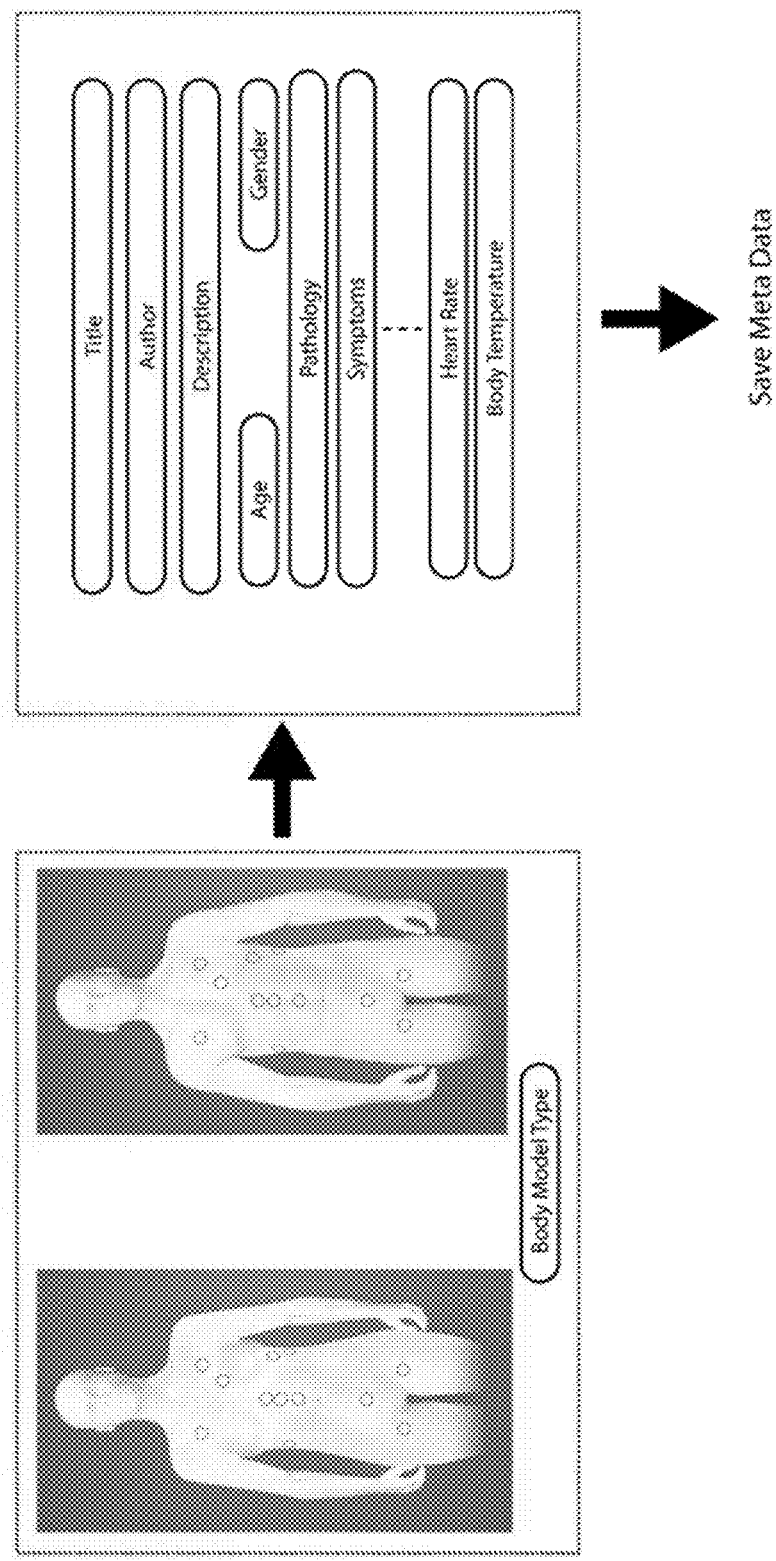
FIG. 2 is a diagram showing the input of meta data using another embodiment of the present invention.
Figure 3:
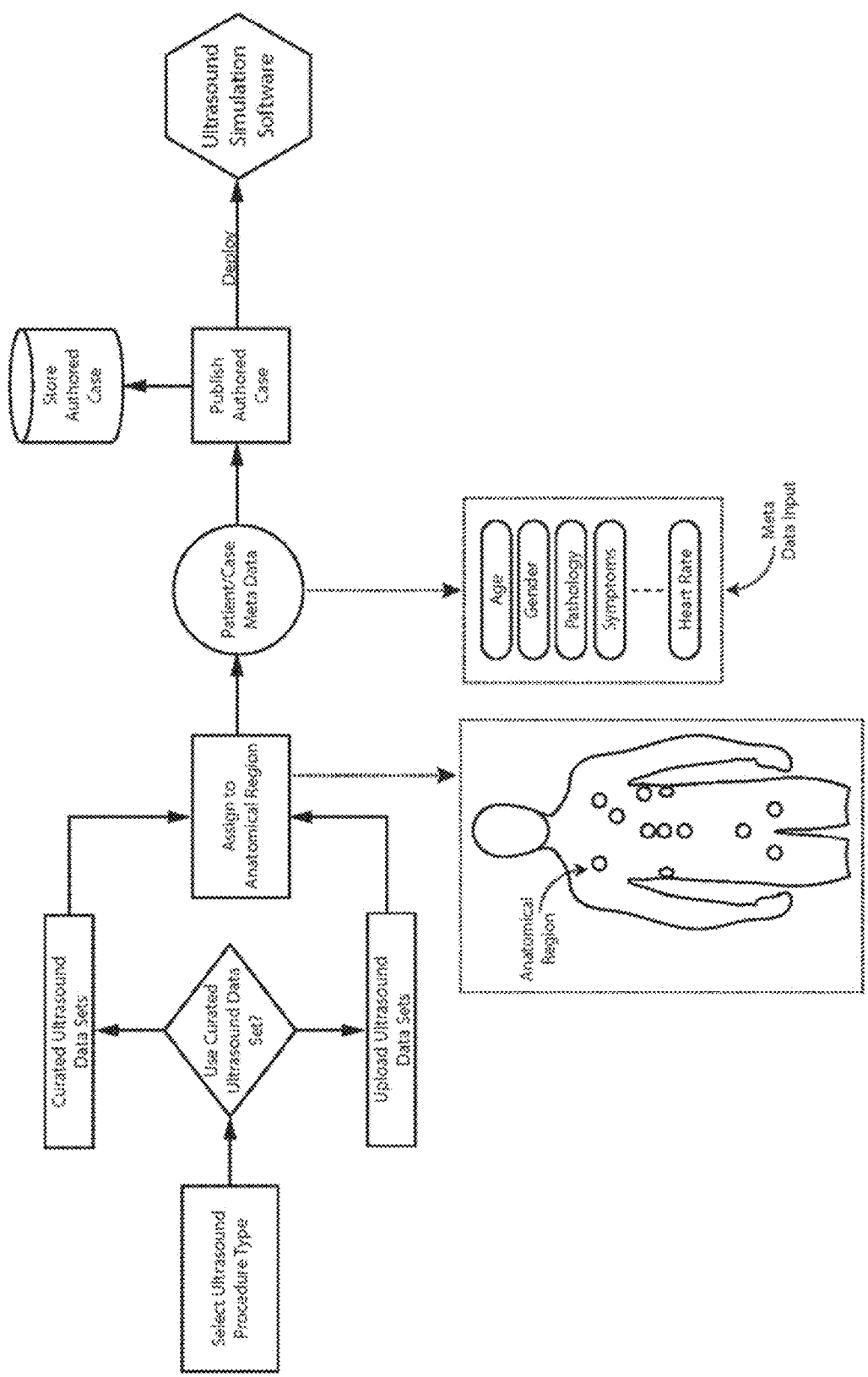
FIG. 3 is a flow chart showing the generation of ultrasound data sets using one embodiment of the present invention.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The process starts with a library of ultrasound data. For the purpose of simulation, ultrasound data should be stored in a 3D or 4D volumetric format, which most modern ultrasound machines are able to acquire. The user may acquire his or her own data sets if he/she has access to the required equipment, or rely on a library of data curated by other parties. If the user wishes to use his/her own data sets, then the service will provide all the tools and guidance required to:

Acquire the data effectively;
Export the data from the ultrasound machine to an exchangeable format;
Import the data into the proposed system; and
Annotate the data with additional information (metadata) to help in finding and authoring the training material in the system.

The collection of volumetric data described thus far shall be referred to in the present application as the volume library. At minimum each item in the volume library, must indicate the location on the body where the volume was acquired and possibly some additional information about the condition of the patient. This is basic information that a medical professional needs in order to understand and interpret an ultrasound case correctly.

The system presents the volume library to the user with a compelling Graphical User Interface (GUI) and a set of visual tools to help in navigating, finding, and selecting a desired subset of volumes. Items in the volume library may be presented to the user by individual representative snapshots, reference sections of the volumetric data, interactive 2D, 3D or 4D visualizations, or a video illustrating the relevant features of the data with optional narration by a curator.

The user proceeds by selecting a collection of volumes that are deemed relevant for a particular teaching purpose, and imports them into a virtual patient, who exemplifies a particular condition or medical scenario. The user can then annotate the condition with a case history that describes various details of the patient including:

The gender, age, and other physical characteristics of the patient;
The condition of the patient during the scanning session;
Values of blood pressure, heart rate, and other relevant clinical readings; and
The presence of pain and other identifiable symptoms.

The user may choose to honor the actual condition of the patient, whose anatomy has been captured by the data set, or attribute an imaginary but plausible set of conditions to the virtual patient that are consistent with the pedagogic purpose of the simulation scenario.

A collection of customized virtual patients will constitute a case library designed by the user to fulfill a particular curriculum of his/her choosing.

The customized case library will be made available to the simulation environment, allowing learners to acquire hands-on experience interacting with the virtual patients in a manner that mimics closely how a medical practitioner would act in the presence of a real patient.

The present invention provides numerous benefits to medical professionals and instructors including:
- The ability to tailor simulation scenarios to the teaching curriculum of medical centers or other types of medical institutions;
- The creation of a large library of cases allowing medical practitioners to acquire hands-on experience with specific and rare types of pathologies;
- The dissemination of simulated content to a wide range of learners over disparate geographical regions; and
- The creation of a community of world experts contributing their knowledge and expertise to improve the quantity and quality of the medical content available to training simulators.

Acquiring and Exporting Custom Data

If the user has access to the appropriate ultrasound equipment, he/she will have the ability to export custom content into the proposed system. The advanced training simulators described in this document require volumetric data sets, which are also the subject of the preferred embodiment, but one skilled in the art can envision a similarly constructed system loaded with 2D images or videos, or entirely different data sets acquired with different imaging tools, such as CT or MRI. Modern ultrasound machine are capable of capturing 3D or 4D data sets with minimal effort. Special ultrasound probes can acquire a dense set of 2D slices at small incremental displacements using an automated internal mechanism. The collection of 2D slices is then processed and registered into a three-dimensional array of data. Alternatively, some systems use an array of piezoelectric transducers to collect a three-dimensional volume with a single scan. More advanced machines used for scanning dynamic organs such as the heart of lungs, can acquire a temporal sequence of 3D volumes, often referred as 4D volumes. Recent progress on the latter allows the acquisition of high quality 4D data sets over multiple cycles of a dynamic organ (e.g. the heart) by reorganizing the acquired data in space and time using a process called Spatio-Temporal Image Correlation (STIC). Recent advances in transducer technology have also explored the use of Capacitive Micromachined Ultrasonic Transducer (CMUT) elements in place of traditional piezoelectric components, yielding imaging, devices with higher resolution and faster response times.

In some cases, it is possible to arrange a collection of 2D scans into 3D volumetric data sets. The latter may impose additional requirements on how the data is acquired, and may require the presence of supplemental motion sensing equipment, but it has the advantage of relying on lower-end ultrasound machines that are found in more disadvantaged parts of the world.

The system will optionally provide visual guides and training materials to help the user acquire the data in the most efficient and effective manner for the purpose of importing the data into a training simulator. These include:

- A protocol for preparing the machine and the patient for the acquisition session;
- How to maneuver the probe to collect the data;
- Which buttons to press to save the image in the required format; and
- What information to preserve on a log book to inform the simulation environment during later stages of customization.

Since many ultrasound machines differ in features and workflows, it may be useful to supplement the afore-mentioned guides with material tailored specifically to selected brands and models of ultrasound machines.

For the purpose of this invention, the user needs the ability to export medical data from the clinical device into a format that can be exported into a computer system provisioned with local or remote storage capabilities.

Most ultrasound machines are able to export data on storage media or directly through a wired or wireless connection. Common storage media include:
- CD-ROM;
- DVD-ROM;
- Flash memory drives;
- External USB hard drives; and
- SD cards.

Modem ultrasound machines often provide the ability to transfer data sets directly to a remote computer using a TCP/IP connection or other network protocol.

Lacking a direct way of exporting data from an ultrasound machine, the present invention can also take advantage of techniques known to those skilled in the art for reconstructing volumetric data sets by assembling frames directly from the video output of the ultrasound machine.

Alternatively, manufacturers could integrate the proposed system into the console and dashboard of the ultrasound machine allowing users to export data directly into the remote system described in this invention.

The proposed system must be able to read and import data in a format that is compatible with training simulators.

Most ultrasound machines are capable of exporting data in the standardized DICOM exchange format, which is preferred for the proposed application. Alternatively lacking support for the DICOM format, some machines may provide other means for exporting data in proprietary formats. To address the latter, implementers may provide special add-ins that allows the system to load and convert such proprietary formats into a known internal format.

Removing Patient Information

HIPAA regulations in the United States, and similar regulations in other countries protect the privacy of patients and prohibit the dissemination of medical information that includes distinct marks or labels that clearly identify their source. For this reason, and to comply with regulations, the proposed system must provide a set of tools and instructions to help the user strip identifying information from the data sets before the upload process, referred to herein as deidentification. Since the process of deidentification may not be fully automated in certain circumstances, the service provider may decide to recruit a committee of reviewers to inspect the data for compliance before approving it for inclusion in the system.

Security

Since the proposed system is designed to host sensitive data, implementers must ensure that the storage solution and all communication channels conform to strict standards of security, access control, and encryption.

User Management

The system needs a mechanism to identify each user or a representative of an interested medical group. The authentication mechanism may rely on the type of username/password credentials widely used by internet services, or may use more sophisticated and secure mechanisms based on two-factor authentication and biometrics. The purpose of this user management system is to associate data sets and custom case libraries with a specific user and to protect their privacy and authorship.

Annotations and Upload

Once the data has been acquired and prepared to be included in the system, the user will log into the system using a designated authentication mechanism and be presented with a friendly portal to upload the data sets, sometimes referred to herein as volume libraries, into a central storage location. Depending on the requirements of the user and service provider, the data sets may be uploaded into a storage node attached to a specific local server, or may be uploaded into a distributed system in the cloud. The portal should also provide custom forms and editing capabilities to annotate the data sets with additional information required by later stages of customization. For instance important annotations that should be included are:

The location on the body where the scan was acquired;
The type of patient;
The condition of the patient during the scan;
The type of ultrasound probe that was used for the acquisition;
The symptoms affecting the patient during the scan;
A brief medical history of the patient if available;
Key vitals measured during the scanning process;
Additional pictures or videos acquired during the scanning process;
The pathology imaged in the scan; and
Search keywords that can help finding the particular scan.

The user may choose to make the uploaded data sets available only to himself/herself, to the general public, or prescribed subsets of other users.

In some cases the user may be unable to upload the data directly into the system through an internet connection or other direct means of data exchange. In such cases, the user may elect to send storage media directly via traditional mail and provide the necessary annotations and information about the user on designated paper forms.

Data Alignment with the Virtual Body

To aid in the correct interpretation of an ultrasound scan, it is very important to know the location on the body where the image was acquired and the orientation of the probe during the scan. As a reflection of this fact, most ultrasound simulators align volumetric data with a rendered 3D body on screen, the virtual body. With this alignment metadata, the training simulator can simultaneously showcase medical data along with the corresponding position and orientation of the probe with respect to the virtual body in the rendered environment.

Unfortunately, most ultrasound machines do not provide the necessary sensor hardware to measure the position and the orientation of the probe with respect of the body automatically during the scan. To complicate the problem, the virtual bodies included in 10 ultrasound simulators also do not match the exact body habitus of the patient, thus a perfect alignment of the medical data with the virtual body is not attainable. Hence, the alignment process must be performed manually and with good judgment to ensure that the expected mismatch between the geometry of the virtual body and the anatomy in the medical data does not mislead the learner.

Given an acquired volume, the proposed system may provide a set of visual tools to Select a virtual body appropriate for the medical data;
Set the position of the volume in 3D space with respect to the virtual body;
Set the orientation of the volume in 3D space with respect to the virtual body; inspect the alignment of the medical data with the geometry of the virtual body;
Alter or deform the geometry of the virtual body to match the medical data more accurately; and
Use additional co-registered data sets, such as CT or MRI scans to aid in the alignment process.

The alignment tools may take advantage of traditional means of input such as mouse and keyboard, rely on trackballs and 3D mice, or use more sophisticated 3-DOF or 6-DOF motion sensing solutions. The process may be further aided by providing the user with more accurate stereopsis and perception of depth using stereoscopic displays or virtual reality headsets.

Given the difficulty of this process the user may choose to forgo the alignment of medical data at the expense of a less immersive simulation experience. Alternatively, the service provider may recruit a team of professionals to perform the alignment for a fee, or allow a crowd-sourced community of volunteers to contribute to the alignment process.

Assigning Data Sets to Virtual Patients

With the volume library populated with medical data, the user proceeds by selecting a subset of volumes and assigning them to a virtual patient. The purpose of this process is to fill an empty virtual body with medical data consistent with a healthy model, a desired pathology, or other medical condition.

The selection process is aided by a rich set of visual tools and an easy-to-use Graphical User interface. The user interface should allow the user to:

View the library of medical data;
Interact with specific medical data sets to explore the anatomy captured in them;
View annotations related to each data set;
View the location of the data sets on the virtual body;
Search for specific data sets that match certain keywords or medical criteria;
Find data sets based on characteristics of the patient such as gender, age, height, and weight; and
Assign the selected data sets to the virtual patient.

Each virtual patient populated with medical data constitutes a medical case. A collection of virtual patients forms a case library.

Authoring Custom Medical Scenarios

For the purpose of training, the system allows the user to embellish each virtual patient additional information describing the condition of the patient, the symptoms, the cause of ailment (e.g. car accident, heart attack, drug overdose), and other details that help provide context for the medical case. The user interface will provide appropriate editing capabilities to accomplish the latter. These may include a variety of computer metaphors used in GUIs, such as:

Edit boxes;
Combo boxes;
Radio buttons; and
Drag-and-drop from a list of existing data.

This additional information is referred to in this application as a case history.

Furthermore, an instructor may prescribe the course of action that is required to diagnose, and treat the patient appropriately by defining a set of available actions and defining the outcome of each. The combination of a populated virtual patient, the case history, and the set of available actions is sometimes referred to herein as a scenario.

In many cases, separate volumetric data sets cannot be integrated in a single virtual patient with plausible outcomes. For instance, it would not make sense to create a virtual patient that contains imaging data for both ovaries and a prostate. While it is generally assumed that a medical learner or practitioner using the system possesses enough knowledge to avoid combining incompatible data sets in a single virtual patient, the system could be greatly enhanced by including a rule engine or other form of fuzzy logic or AI that checks and verifies the degree of compatibility of different data sets and guides the user in only selecting content that results in plausible medical cases. For instance, the system may exclude organs specific to male subjects, if the user has specifically chosen to author a pregnancy case. Expert systems of this kind have been implemented and deployed in other domains, and it is therefore reasonable to expect an individual skilled in the art to have the ability to implement the latter without further guidance.

An alternative embodiment involves integrating the scenario into a larger physical mannequin. The end user would scan through the imported data sets and work through the scenario using a physical mannequin as the scanning surface, rather than a virtual patient.

Using the Case Library in Training Simulators

In designing the system care must be taken to define the case library and scenarios in a way that is compatible with at least one leading training simulator. The proposed system will have the ability to make the entire custom case library authored by the user available in the training simulator. The training simulator in turn is expected to provide the following capabilities to the user:

View the available case library and select a desired case;
Show the virtual body matching the selected case;
Position the medical probe on a desired location on the virtual body;
Scan the virtual body in the simulated environment and view the associated medical data;
View the case history for the virtual patient; and
Perform actions according to the scenario prescribed by the author of the medical case.

In an alternative embodiment, the case authoring functionality may be embedded directly within a training simulator. In this case the training simulator operates in two distinct modes:

(1) Case authoring mode. Allows the user create custom content possibly leveraging the existing case library provided by the simulator
(2) Simulation mode. Allows the user browse the available sets of medical content, which can include curated content by the vendor, curated content professionally made by third panics, custom content created by the user, and optionally custom content made by other users. Once selected, the user can interact with the medical content using the features provided by the training simulator.

A typical workflow for a learner using the training simulator may proceed as follows:

(1) Log into the training simulator with the appropriate credentials provided by the system administrator;
(2) Once logged in, the training simulator will show a portion of the case library consistent with the access rights set in the system for the current user;
(3) Navigate the case library to find a case matching the intent of the learner;
(4) Select the desired case, and start reading the provided case history;
(5) Establish a strategy for diagnosing the patient;
(6) Position the virtual probe on the correct location of the virtual body in the simulated environment;
(7) Scan the virtual patient and try to formulate a diagnosis based on the evidence presented in the medical data;
(8) Move the virtual probe to a different location on the virtual body to gather more evidence about the possible ailment of the patient;
(9) Once satisfied with the study, proceed by selecting one of the available actions prescribed by the scenario to treat the patient; and
(10) Get a report as to whether or not the treatment provided has helped the patient survive the ailment.

It is understood that the proposed workflow is just an illustration of the basic user experience in the preferred embodiment. One may construct a system consistent with the spirit of this invention by skipping, reordering, or adding more steps to the proposed workflow.

Deployment and Architecture

The proposed system may be implemented most naturally with a server-oriented architecture consisting of a server and multiple clients. The server has the following responsibilities:

Manage user accounts;
Store the case libraries for all users;
Provide the ability to upload data into the system;
Provide a centralized interface for clients to author their custom case library;
Provide a dashboard for users to manage their content and access rights;
Provide visual guidance and instruction material to help users interact with the system;
Provide a back-end for training simulators to load and use custom case libraries in the simulated environment;
Provide additional tools for the conversion, deidentification, and annotation of medical data; and
Provide additional tools to manage the licensing and distribution of content.

The server functionality may be located on single physical server restricted to a local network, on a data center managed by a single vendor, or on a geographically distributed cloud.

The clients can be any computing devices with an internet connection or a physical connection to a designated local server. The client will connect to the server and have the ability to:

Log-in into the server;
Upload data into the server;
Access the dashboard for his/her user account;
Access training material describing how to use the system;
Access the user interface for viewing, selecting, and authoring the custom case library; and
Managing licenses and the distribution of content.

In the preferred embodiment the server delivers the content and interactive capabilities with established web technologies. Alternatively, all the client functionality will be provided by a specialized desktop or mobile application than can connect and exchange data with the server remotely. In the preferred embodiment the means of communication between the client and server is provided by the established internet infrastructure and protocols such as TCP/IP, but the implemented may decide to use proprietary solutions to achieve better security, efficiency, and control over the system.

In some environments and institutions, especially in high-security facilities with strict security policies, a client-server architecture is not feasible. If needed, the entire system described in this invention can be implemented on a single designated machine storing all the required content, software, and simulation functionality. Alternatively, the same client-server architecture can be deployed on a designated server restricted to a local network.

While the present invention has been described with regards to particular embodiments, including focusing on the use of volumetric data sets of ultrasound data, the same invention can be carried out with volumetric data sets originating from other imaging technologies such as CT or MRI, and it is further recognized that additional variations on the concepts of the present invention may be devised without departing from the inventive concept.

What is claimed is:

1. A computer-based ultrasound simulation system, comprising:
   a) a plurality of simulation cases derived from real-patient volumetric data sets from different patients, each simulation case comprising information regarding case histories and realistic sets of available actions;
   b) a graphical user interface configured to display a virtual body, the virtual body comprising a plurality of predetermined discrete anatomical regions displayed on the virtual body;
   c) a volume library stored on a server, the volume library comprising the volumetric data sets from the different patients for assigning to the plurality of discrete anatomical regions displayed on the virtual body to create the plurality of simulation cases; and
   d) a processor configured to select the plurality of predetermined discrete anatomical regions, select the volumetric data sets from the volume library, and assign one of the volumetric data sets to one of the discrete anatomical regions, wherein
   a first volumetric data set is assigned to a first predetermined discrete anatomical region in the virtual body and a second volumetric data set is assigned to a second predetermined discrete anatomical region in the virtual body, wherein the first volumetric data set is from a different patient than the second volumetric data set, and wherein the first volumetric data set is discontinuous from the second volumetric data set.

2. The system of claim 1, wherein the first and second volumetric data sets are acquired from an imaging technology, the first and second volumetric data sets selected from the group consisting of 3D volumetric data and 4D volumetric data, wherein each of the first and second volumetric data set occupies a volume in the virtual body from different patients.

3. The system of claim 2, wherein the processor is configured to further display alignment tools on the graphical user interface for aligning each of the first and second volumetric data sets within the virtual body.

4. The system of claim 3, wherein the processor is configured to further display an item representing one of the first or second volumetric data sets for assignment to the predetermined discrete anatomical region on the virtual body, wherein the item is selected from the group consisting of a representative snapshot, sections of the volumetric data, interactive visualizations, and a video clip.

5. The system of claim 4, wherein the video clip comprises an audio track to store a narration of the volumetric data sets.

6. The system of claim 2, wherein the imaging technology is an ultrasound machine.

7. The system of claim 2, wherein the first and second volumetric data sets are annotated with case histories.

8. The system of claim 1, further comprising an ultrasound training simulator to run an ultrasound simulation based on the plurality of simulation cases uploaded to the system.

9. The system of claim 8, further comprising a case authoring mode for adding medical data into the volume library, and a simulation mode for simulating an ultrasound based on the plurality of simulation cases, wherein the case authoring mode is configured to edit the information of the plurality of simulation cases.

10. The system of claim 1, further comprising visual tools configured to allow for selection of the virtual body and alter a geometry of the virtual body.

11. A computer-based ultrasound simulation system, comprising:
   a) a plurality of simulation cases derived from real-patient volumetric data sets, each simulation case comprising information regarding case histories and realistic sets of available actions;
   b) a graphical user interface displaying a virtual body, the virtual body comprising a plurality of predetermined discrete anatomical regions displayed on the virtual body;
   c) a volume library stored on a server, the volume library comprising the volumetric data sets for assigning to the plurality of predetermined discrete anatomical regions to create the plurality of simulation cases;
   d) alignment tools displayed on the graphical user interface for aligning each volumetric data sets within the virtual body, wherein the graphical user interface displays an item representing one of the volumetric data sets, the item selected from the group consisting of a representative snapshot, sections of the volumetric data, interactive visualizations, and a video clip for selecting the one of the volumetric data sets, wherein the video clip comprises an audio track to store a narration of the volumetric data sets, volumetric data sets are annotated with case histories;
   e) an ultrasound training simulator to run an ultrasound simulation based on the plurality of simulation cases uploaded to the system;
   f) a case authoring mode for adding medical data into the volume library, and a simulation mode for simulating an ultrasound based on the plurality of simulation cases, wherein the case authoring mode is configured to edit the information of the plurality of simulation cases;
   g) visual tools configured to allow for selection of the virtual body and alter a geometry of the virtual body; and
   h) a rule engine configured to check compatibility of each volumetric data for the virtual body selected to maintain anatomically plausible medical cases,
   i) wherein a processor is configured to display the volume library, select a first discrete anatomical region from the plurality of predetermined discrete anatomical regions displayed on the virtual body, select a first volumetric data set from the volume library, assign the first volumetric data set to the first discrete anatomical region, wherein an appearance of the first discrete anatomical region changes when assigned the first volumetric data set, select a second discrete anatomical region, select a second volumetric data from the volume library, and assign the second volumetric data set to the second discrete anatomical region, wherein the first volumetric data set and the second volumetric data set are acquired from different patients, and wherein the first volumetric data set is discontinuous from the second volumetric data set.

\* \* \* \* \*